United States Patent
Etter et al.

(10) Patent No.: US 8,652,387 B2
(45) Date of Patent: Feb. 18, 2014

(54) ADMINISTERING DEVICE WITH A MULTI-COMPONENT INJECTION-MOLDED HOUSING

(75) Inventors: Philip Etter, Ittigen (CH); Marco De Polo, San Mateo, CA (US)

(73) Assignee: Roche Diagnostics International AG, Steinhausen (CH)

( * ) Notice: Subject to any disclaimer, the term of this patent is extended or adjusted under 35 U.S.C. 154(b) by 0 days.

(21) Appl. No.: 13/406,887

(22) Filed: Feb. 28, 2012

(65) Prior Publication Data
US 2012/0153534 A1   Jun. 21, 2012

Related U.S. Application Data

(62) Division of application No. 11/343,973, filed on Jan. 31, 2006, now Pat. No. 8,147,460.

(51) Int. Cl.
*B29C 45/14*   (2006.01)
(52) U.S. Cl.
USPC ........ 264/294; 264/254; 264/255; 264/271.1; 264/279; 264/279.1; 604/48; 604/65
(58) Field of Classification Search
USPC ........... 264/254, 255, 294, 271.1, 279, 279.1; 604/65, 48
See application file for complete search history.

(56) References Cited

U.S. PATENT DOCUMENTS

| | | | | |
|---|---|---|---|---|
| 4,346,511 A | * | 8/1982 | Jones et al. | 29/458 |
| 5,370,622 A | * | 12/1994 | Livingston et al. | 604/151 |
| 5,578,802 A | * | 11/1996 | Palmowski | 200/5 A |
| 5,733,493 A | * | 3/1998 | Katsuno et al. | 264/255 |
| 6,305,908 B1 | | 10/2001 | Hermann et al. | |
| 6,423,035 B1 | | 7/2002 | Das et al. | |
| 2004/0024364 A1 | * | 2/2004 | Langley et al. | 604/187 |

* cited by examiner

Primary Examiner — Joseph S Del Sole
Assistant Examiner — Lawrence D Hohenbrink, Jr.
(74) Attorney, Agent, or Firm — Dinsmore & Shohl LLP (57) ABSTRACT

Method of producing an administering device for infusing or injecting a product, whereby in order to mold a housing shell serving as a case for components of the administering device in a multi-component injection molding process at least one pre-molded, transparent insert part made from a first plastic material is inserted in an injection mold molded to a shape matching the shape of the housing shell, a dimensionally stable, curable second plastic material is injected into the injection mold around the insert part to render it watertight and an opening left free in the second plastic material is closed to render it watertight by injecting on an elastomeric third plastic material.

20 Claims, 4 Drawing Sheets

Fig. 6 ated by the invention, a housing shell of the administering device is produced in a multi-component injection molding process. The housing shell serves as a case for components of the administering device, in particular mechanical and electronic components which are sensitive to moisture. However, the housing shell not only serves as a case for these components and protects them from external influences, especially moisture, it also fulfills additional functions insofar as it affords visibility of one or more components or allows control elements to be operated. In this sense, it is a multi-functional housing shell with wall regions of different properties in order to fulfill the different functions. As a whole, the housing shell is dimensionally stable to the degree that it is capable of withstanding the type of mechanical stress which can be expected during operation. It also has at least one transparent wall region and at least one flexible wall region, one of which provides visibility, whilst the other enables a control element to be operated. The housing shell is also watertight over the relevant wall regions.

ADMINISTERING DEVICE WITH A MULTI-COMPONENT INJECTION-MOLDED HOUSING

CROSS-REFERENCE TO RELATED APPLICATIONS

This application is a divisional of application Ser. No. 11/343,973, filed Jan. 31, 2006.

TECHNICAL FIELD

Embodiments of the invention relate to an administering device for infusing or injecting a product, preferably a liquid medicament, such as insulin for example, and a method of producing the administering device, as far as its housing is concerned.

BACKGROUND

In many applications for which administering devices are used, the demands placed on them in terms of water tightness are high. This is of particular importance in situations where drugs are self-administered, as is common practice in the case of treatment for diabetes, for example. In terms of their external dimensions, administering devices have now become so small that they can be carried in virtually every day to day situation, for example during sport, whilst showering and even in water. Under all circumstances, it must be possible to guarantee water tightness under the conditions which can be anticipated during the time leading to the expiry date, and administering devices are designed to be serviceable for several months or even years. Water tightness is problematic because the housings of administering devices are not only required to protect moisture-sensitive components from moisture, but must also fulfill other functions. For example, it must be possible to use a key pad, which is itself sensitive to moisture or is at least connected to moisture-sensitive components. It must also be borne in mind that a visual, acoustic or tactile indicator, for example a vibrating display, also has to be protected from moisture. In the case of a visual indicator or display, the reader must be able to read the functions presented on the display through a transparent see-through region.

As a rule, the housings of administering devices therefore have openings, in which flexible or transparent wall elements are inserted. In order to guarantee water tightness, the wall elements are adhered along the edge of the respective opening to an otherwise watertight shell structure of the housing or are joined by ultrasound welding or some other means. In addition to molding the housing structures, namely the shell structure and the wall elements which have to be inserted, the process of manufacturing the housings requires other joining operations, namely the insertion of the relevant wall elements followed by their connection by means of another joining technique, such as bonding or welding for example. The additional joining process incurs costs and constitutes new sources of faults, which can lead to faults in the seal and in any event, increases the amount of work involved in quality assurance.

DETAILED DESCRIPTION

One objective of the invention is to guarantee greater reliability of an administering device with a multi-functional housing in terms of its water tightness.

As proposed by the invention, a housing shell of the administering device is produced in a multi-component injection molding process. The housing shell serves as a case for components of the administering device, in particular mechanical and electronic components which are sensitive to moisture. However, the housing shell not only serves as a case for these components and protects them from external influences, especially moisture, it also fulfills additional functions insofar as it affords visibility of one or more components or allows control elements to be operated. In this sense, it is a multi-functional housing shell with wall regions of different properties in order to fulfill the different functions. As a whole, the housing shell is dimensionally stable to the degree that it is capable of withstanding the type of mechanical stress which can be expected during operation. It also has at least one transparent wall region and at least one flexible wall region, one of which provides visibility, whilst the other enables a control element to be operated. The housing shell is also watertight over the relevant wall regions.

The word "or" as used in this application, i.e. in the claims and the description, should always be construed in the usual logical sense as meaning "and/or", except where it is obvious from the respective context that it is intended to have a restrictive meaning in the sense of "and" or "either or".

As proposed by the invention, a multi-functional housing shell of this type is molded in a multi-component injection molding process. The at least one transparent wall region is made by means of a pre-molded, transparent insert part, around which a dimensionally stable, curable plastic material is injected to render it watertight. This is done in an injection mold. In order to obtain the flexible wall region, care is taken to ensure that at least one opening is left free in the dimensionally stable, curable plastic material. In order to seal the opening to render it watertight, an elastomeric plastic material is injected onto it, preferably a thermoplastic elastomer.

In view of the fact that the housing shell is produced uniformly by injection molding with different plastic materials, each of which can be selected so that it is best suited to the special function, the multi-functional housing shell can be produced by molding, namely by injection molding, and does not require any joining process which may be susceptible to faults. A housing shell can be made using only the different plastic materials that are unavoidable in any event, without having to use additional adhesive substances. The seal in the regions where the different plastic materials are connected can be guaranteed with a high degree of reliability. The dimensionally stable, curable plastic material constitutes the skeleton of the housing shell and in particular is capable of withstanding the usual mechanical stress, including impact stress. The wall regions of the housing shell made from this plastic material can be assumed to be non-deformable for practical purposes and in this sense dimensionally stable.

The dimensionally stable, curable plastic material and the flexible plastic material can be injected into the injection mold simultaneously in a co-injection process. However, it is preferable if the flexible plastic material is not injected until later in a bonding injection molding process. At the time as the latter is injected on, the dimensionally stable, curable plastic material has preferably set to the degree that the shape of the housing shell is already fixed. The temperature during the injecting-on process should be higher than room temperature. Heating may be applied to achieve the higher temperature. More preferably, the flexible plastic material is injected on before the dimensionally stable, curable plastic material reaches room temperature during the setting process.

When molding the flexible wall region during the subsequent injection, the opening in the dimensionally stable, curable plastic material is produced by a filler or if necessary several fillers, which is or are placed at the appropriate point in the injection mold before the dimensionally stable, curable plastic material is injected in. Once the dimensionally stable, curable plastic material has set or has at least partially set, the injection mold is opened and the filler or the several fillers are removed. Ready-molded in this manner, the housing shell, which nevertheless still incorporates the at least one opening, can be removed from the injection mold and placed in an injection mold for injecting on the elastomeric plastic material. More preferably, however, the injection mold is also used for injecting on the elastomeric plastic material, i.e. it is closed again after removing the filler. In a first variant of the method, the injection mold has a nozzle for the elastomeric plastic material, which is closed when injecting around the at least one insert part and is then opened so that the elastomeric plastic material can be injected into the injection mold to cover the full surface of the opening so that it lies against the cured plastic material along the edge of the opening and in this sense is injection molded on. In a second variant of the method, the injection mold has a removable mold piece which is only used for injection molding the elastomeric plastic material. Again in the second variant, the already molded housing shell, still incorporating the at least one opening, is left in the injection mold. A mold part of the injection mold that was previously used when injection molding around the insert parts is replaced by the removable mold part, which has an injection nozzle for the elastomeric plastic material in the region of the opening produced by the filler and naturally has a negative shape to the flexible wall region to be formed.

The housing shell obtained after the injecting-on process still has an opening, which is big enough to allow components to be accommodated in the housing shell to be introduced through the opening and fitted. Once the relevant components have been fitted, the opening is sealed by means of another housing shell, rendering it watertight. On the same date as this application, the applicant filed another application entitled, "Self-sealing connection for housing shells of an administering device", which discloses the watertight connection between the two housing shells. For details of this connection and the rest of the housing shell, reference may be made to this other application.

The invention further relates to an administering device with a housing shell produced by the multi-component injection molding process proposed by the invention. The administering device comprises the housing shell, a receiver formed in the housing shell for a product to be administered, a driver mechanism for driving the product and at least one control element for controlling a visual display, for example, for influencing the driver device or some other control function. The receiver formed by the housing shell is filled or may be filled directly with the product so that the housing shell itself forms a product container. Preferably, however, a container for the product, for example an ampoule, is or can be accommodated in the receiver. The conveying mechanism may comprise a plunger which can be moved in the product container and a plunger drive.

The housing shell has a transparent wall region made from a first plastic material, a dimensionally stable shell structure made by injection molding using a different, second plastic material forming the side walls of the housing shell, and a flexible wall region made from a third plastic material. The transparent wall region is formed by an insert part, which is injected around by the second plastic material by the method outlined above. The second plastic material corresponds to the dimensionally stable, curable material and the third plastic material is flexibly resilient, preferably a thermoplastic elastomer. The housing shell is molded from the plastic materials in the injection mold so that the three different wall regions already described above, each according to their functions, are connected in a watertight fit, thereby resulting in a watertight housing shell. The water tightness is achieved on the basis of a material join, a non-positive fit or a form fit, preferably a combination of at least two of these connection types. The at least one transparent wall region, i.e. the at least one insert part, as well as the at least one elastic wall region in some advantageous embodiments are joined to the second plastic material, i.e. the hard shell material, both by a material join and by a form fit.

In preferred embodiments, the first, second and third plastic materials may each be a material from the same family of plastics, e.g. a polyamide PA. Another advantageous combination is one in which PA is used as the first and the second plastic materials and SEBS is used as the third plastic material. In principle, the materials may also be from three different families of plastics.

In preferred embodiments, the flexible wall region is of a three-dimensional structure. If it covers an access for a control element, it preferably has an indentation on the outside, into which the control element projects. The flexible wall region advantageously conforms to the shape of the control element. The control element may be a push button in particular. The flexible wall region may overlap a control field incorporating several control elements and in these embodiments it is advantageously of a three-dimensional structure adapted to the shape of the control elements, i.e. is provided with several indentations.

The transparent insert part may be a flat or cambered viewing window, for example a display window. The transparent wall region may also be a wall region of the holder for the product, to permit a visual control of how full the product container is. In an embodiment of this type, the insert part may be tubular in shape, for example, with an approximately circular cross-section, or alternatively with any other cross-section, and may form a major part or the entire part of the side wall of the receiver for the product.

Advantageous features and combinations of features are also described in the dependent claims. The features described above and those defined in the dependent claims and their combinations are mutually complementary and interchangeable.

An example of an embodiment of the invention will be explained below with reference to the appended drawings. Features which become apparent from the embodiment described as an example advantageously supplement the subject matter of the claims, each individually and in every combination of features, as do the embodiments described above. Of the drawings:

Figure 1:
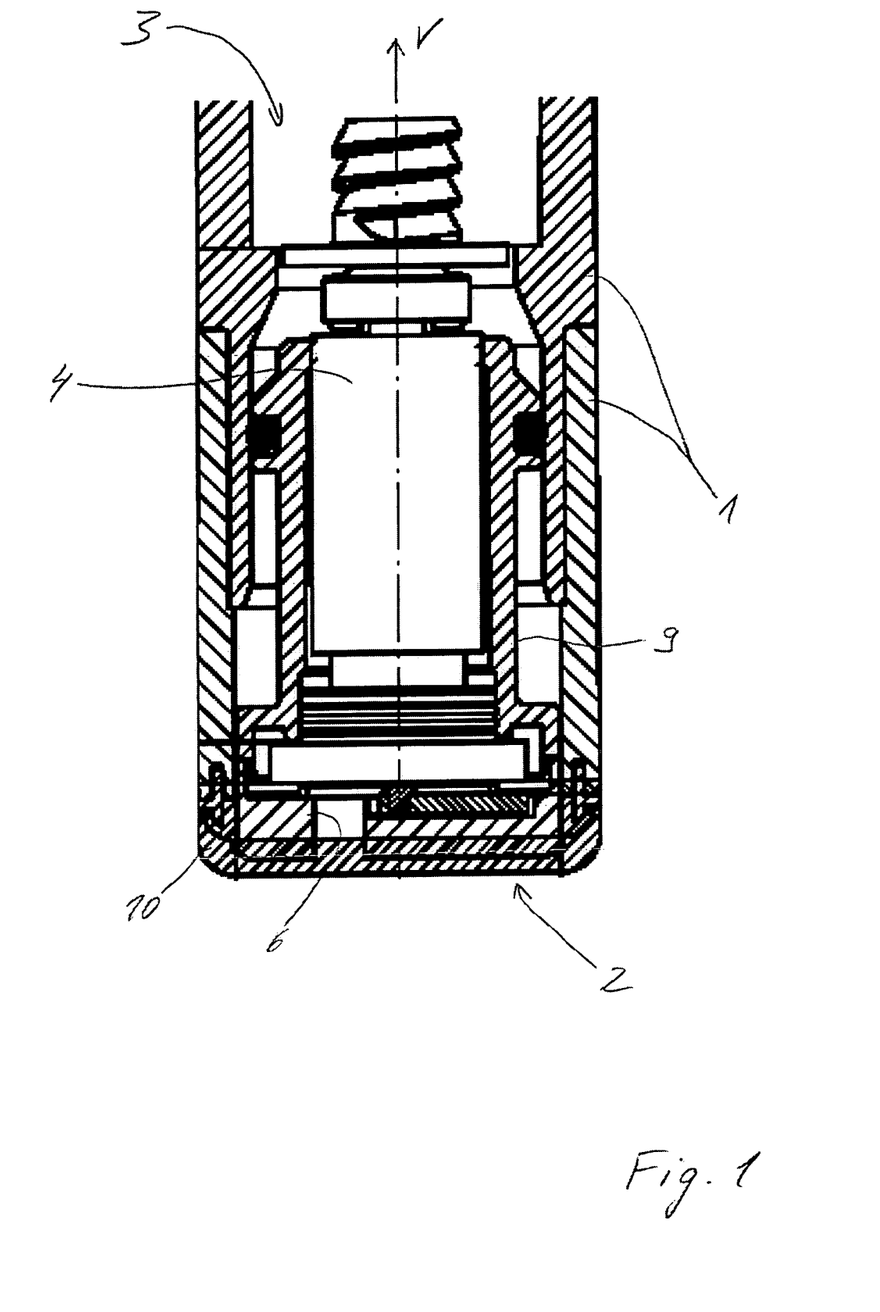
FIG. 1 is a longitudinal section showing part of an administering device.

FIG. 1 is a longitudinal section illustrating a part of an administering device. The administering device is an infusion device for infusing insulin, for example. The infusion device is compact and lightweight so that it can easily be carried in or under the clothing. Apart from the characterizing features proposed by the invention, the infusion device may correspond to standard infusion devices used for self-administration, for example insulin pumps.

The infusion device has a housing comprising a first housing shell 1 and a second housing shell 2, which, in the joined state illustrated, form a watertight case for moisture-sensitive components of the infusion device. Housing shell 1 specifically forms a receiver 3 for a product container, which is preferably an ampoule, filled with a product to be administered, for example insulin, of the type used for the treatment of diabetes or other treatments where the patient administers the relevant drug himself. In FIG. 1, the receiver 3 is empty, i.e. there is no product container inserted. The first housing shell 1 also encloses a driver mechanism 4, by means of which the product can be conveyed out of the product container. In particular, the driver mechanism 4 may be a plunger driver with a plunger which can be moved in the product container in a forward drive direction V and a drive mechanism for driving the plunger forward.

The housing shell 1 forms the side wall of the housing 1, 2, but is open at a bottom end face across its entire internal cross-section. The components to be disposed in the housing 1, 2, in particular the driver mechanism 4, can be introduced into the housing shell 1 through the resultant opening and fitted during assembly of the infusion device. Housing shell 2 closes the terminal opening of housing shell 1 in a watertight arrangement and in the connected state forms the base of the housing 1, 2.

The housing shell 2 comprises several parts, although the several parts are connected to one another to form a solid unit. Housing shell 2 comprises a dimensionally stable support structure 6 and a seal 10, which form the base of the housing 1, 2, and a holder 9 projecting from the support structure 6 into the housing shell 1 for the driver mechanism 4. The support structure 6 and the holder 9 are formed from the same dimensionally stable, curable plastic material. The seal 10 is injection-molded onto the support structure 6. The seal 10 is made from a thermoplastic elastomer. The support structure 6 and the seal 10 are joined to one another in a form fit and by a material join. The support structure 6 and the holder 9 are joined to one another in a form fit and a non-positive fit. The support structure 6 is formed by an injection molding process and the seal 10 is injected around it. Accordingly, due to the multi-component injection mold process, a particularly solid joint is obtained between the support structure 6, which constitutes a hard component, and the seal 10 in the form of a soft component.

Figure 2:
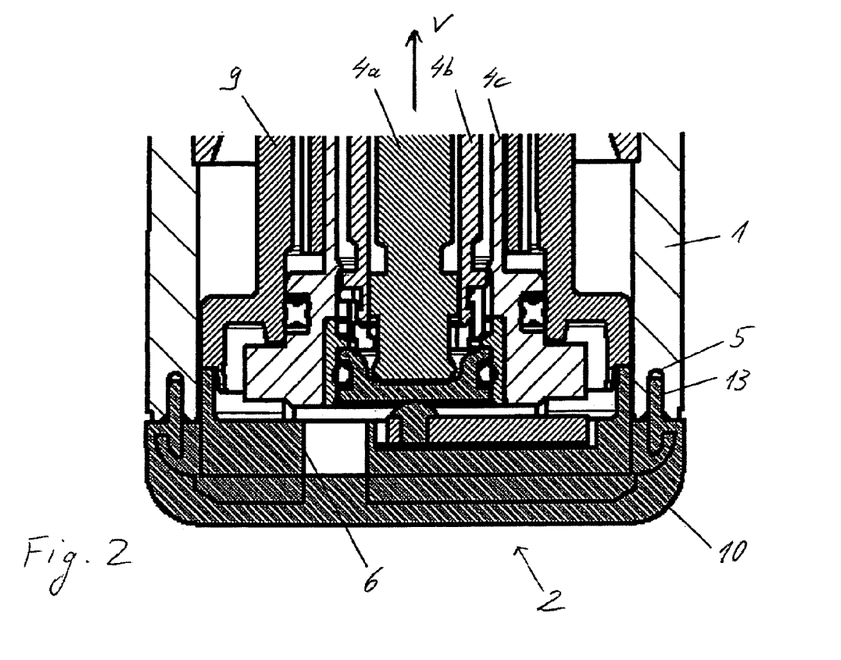
FIG. 2 shows the region where two housing shells of the administering device are joined.

FIG. 2 illustrates the base region of the injection device, in particular the region where the housing shells 1 and 2 are joined, as well as an example of a driver mechanism 4. The driver mechanism 4 comprises a central plunger rod 4a, a central drive member 4b coaxially surrounding the plunger rod 4a and an outer drive member 4c coaxially surrounding the drive member 4b. The drive members 4b and 4c are provided in the form of drive sleeves. The plunger rod 4a and the central drive member 4b engage by means of a thread so that the plunger rod 4a is moved axially in the forward drive direction when the drive member 4b is driven in rotation. The drive members 4b and 4c engage with one another by means of another thread. Together, the plunger rod 4a and the drive members 4b and 4c form a telescopic drive unit for the plunger and, in conjunction with the plunger, the driver mechanism 4. Examples of such telescopic driver mechanisms are described in patent specifications U.S. Ser. No. 09/403,443 and EP 0 991 440 B1, which are included herein by way of reference.

The drive member 4c is axially supported on the support structure 6 in the direction opposite the forward drive direction and, in the embodiment illustrated as an example, the drive member 4c is supported on an axially protruding projection, formed in the central region of the support structure 6. The drive member 4c is supported on the holder 9 in the forward drive direction V and transversely thereto in the radial direction.

The housing shells 1 and 2 are joined to one another by means of a self-sealing connection. The self-sealing connection exists directly between the housing shell 1 and a sealing lip 13 of the seal 10. The sealing lip 13 projects axially from an end face of the seal 10 facing the housing shell 1, i.e. vertically. A seal gap 5 is formed in the housing shell 1 at its terminal end, which opens at the end face of the housing shell 1 facing the end face of housing shell 2. The seal gap 5 projects axially out from its orifice in the end face into the housing shell 1. The seal gap 5 and the sealing lip 13 are each formed so that they extend continuously around a central axis pointing in the forward drive direction V and are in axial alignment with one another. The sealing lip 13 is pressed into the seal gap 5 and establishes a pressing contact with each of the oppositely lying, mutually facing side walls of the seal gap 5. The relevant side walls of the seal gap 5 are parallel with one another and with the forward drive direction V of the driver mechanism 4.

Figure 3:
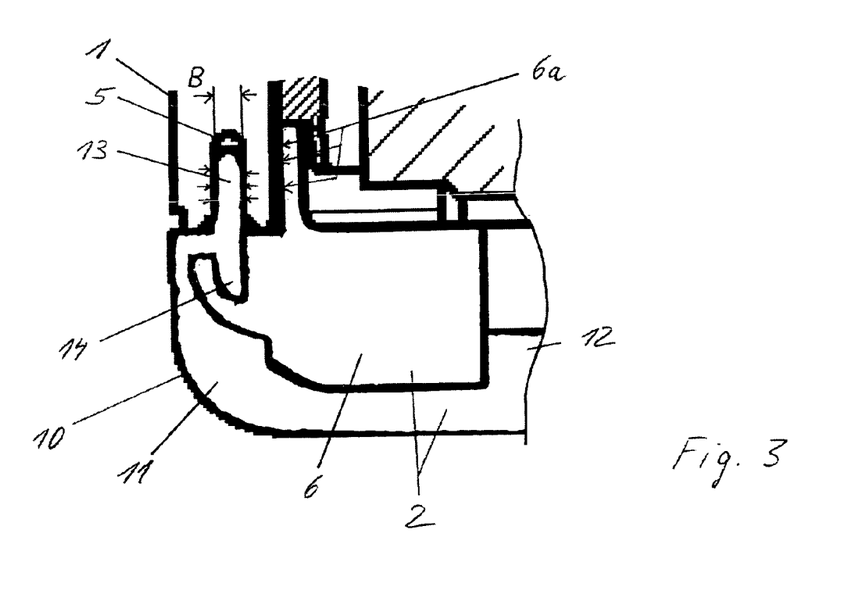
FIG. 3 shows a detail of the joining region.

FIG. 3 is a diagram illustrating a point of the self-sealing connection on a larger scale than FIG. 2. The hatching of the support structure 6 and the seal 10 have been omitted solely for the sake of clarity.

The seal gap 5 has a gap width B of a few tenths of a millimeter extending all around it. The manufacturing tolerance of the seal gap 5 with respect to the gap width B is correspondingly small. The manufacturing tolerance is smaller than the standard dimension by at least one order of magnitude, i.e. by at least a factor of 10. If the standard dimension for the gap width B is 0.2 mm, for example, the tolerance is therefore ±0.02 mm, for example. The sealing lip 13 has over size in comparison to the gap width B, so that it is compressed in the narrower seal gap 5 when pressed in and sits in pressing contact with the side walls of the seal gap 5. The pressing pressure bearing on the contact surfaces of the sealing lip 13 is indicated by several small arrows.

The seal 10 is disposed on the external face of the support structure 6 and surrounds the support structure 6, lying tightly against it like a sheath. Consequently, the seal 10 not only forms the sealing lip 13 but also has a shell region 11 which forms a bottom face of the housing shell 2 and hence the housing 1, 2. The shell region 11 is so thick and the material of the seal 10 so soft that the seal 10 also acts as a damping means and anti-slip means on the bottom face of the housing 1, 2. The shape of the seal 10 is akin to that of a flat pan. It extends from the bottom face across its outer peripheral region as far as a top face of the support structure 6 and engages round an outer peripheral edge on the top face of the support structure 6. To obtain an even firmer form fit, it not only engages round the support structure 6 but also engages behind the support structure 6 by means of an anchoring element 14 lying axially opposite the sealing lip 13 and projecting towards the bottom face. Accordingly, the support structure 6 has a recess on its top face, in which the anchoring element 14 is accommodated. In the embodiment illustrated as an example, the recess in the support structure 6 is provided in the form of a peripheral groove and the anchoring element 14 on the seal 10 is provided in the form of a peripheral protuberance similar to the sealing lip 13. Since the seal 10 engages round the support structure 6 and advantageously also engages behind it, a non-positive fit is also obtained between the support structure 6 and the seal 10 in addition to the form fit, because the plastic material from which the seal 10 is made confines the support structure 6 after the injection process. In a central region, the support structure 6 also has an orifice or recess, into which the seal 10 projects by means of a base 12, which completely fills the recess or orifice of the support structure 6. As a result, an additional anchoring is obtained for the support structure 6 in the central region of the seal 10.

The support structure 6 not only acts a support frame for the seal 10 as such, but also as an axial support for the sealing lip 13. To this end, the support structure 6 extends outwards beyond the seal gap 5. The support structure 6 therefore also serves as a stop, by means of which housing shell 2 sits in contact with housing shell 1 in the axial direction in the connected state, so that the axial position of housing shell 2 relative to housing shell 1 is exactly defined when in contact. The relevant end face of the support structure 6 lies opposite the part of the end face of the housing shell 1 which internally adjoins the orifice of the seal gap 5. The part of the end face of housing shell 1 externally adjoining the orifice of the seal gap 5 lies opposite an end face of the seal 10 and is preferably pressed into this end face of the seal 10 with a slight pressing pressure.

In addition to the pressed joint obtained by means of the sealing lip 13, the housing shells 1 and 2 are also non-detachably connected to one another by means of a material join. The material join is obtained by bonding. The region of the material join 6a, which in the embodiment illustrated as an example is a bonded region, extends peripherally along a casing internal face of the housing shell 1 adjoining the end face of the housing shell 1 and a casing external face of the support structure 6 adjoining it in a non-positive fit.

Figure 4:
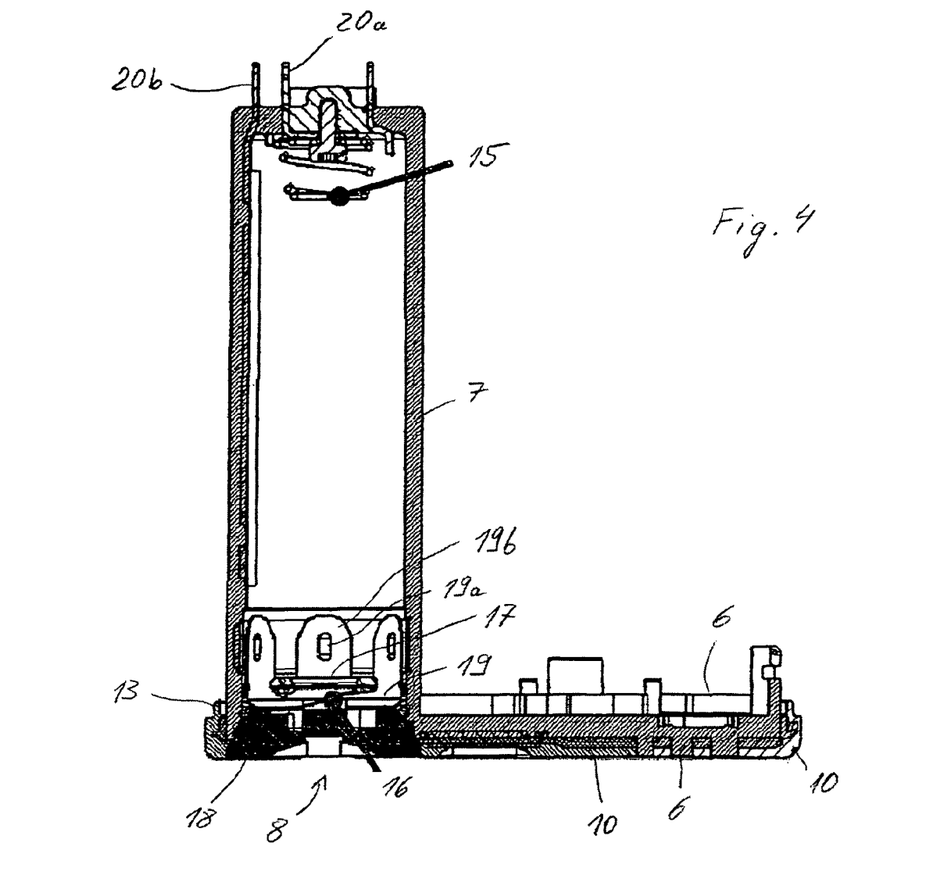
FIG. 4 shows one of the housing shells with a battery compartment.

FIG. 4 is a diagram in section illustrating the compartment 7 of a device for injecting or infusing a product, in which a power source, e.g. a cylindrical battery, can be inserted. The compartment 7 is manufactured in a single piece with the bottom part of the device, e.g. during the injection molding process. In its bottom face, the compartment 7 has an access opening 8, by means of which the power source can be inserted in the compartment and removed from the compartment. This option is provided because the device may be designed for a longer service life than the power source, which will then have to be replaced whenever necessary. The shape of the compartment 7 for the power source is such that the compartment 7 affords a reliable lateral guiding action for the power source, making it easy to insert the power source.

The access opening 8 can be closed by means of a cover 18. This cover 18 is designed to close off the compartment 7 rendering it watertight because penetration of the compartment by moisture can cause the power source to short-circuit. In order to obtain a high quality seal, the cover 18 is provided in the form of a screw-on cap and also has a sealing ring 26, which is pressed against an internal wall of the compartment 7 when the cap 18 is screwed on.

Disposed at the top end of the compartment 7 is a first contact 15, against which one terminal of the power source can be pushed. The contact is provided in the form of a contact spring 15, which means that it can be elastically compressed when biased by the power source in its insertion direction and spring back into its initial position when no longer biased. The contact spring 15 itself may form an electric down conductor or is connected to a down conductor 20a. The power source is connected to a consumer, e.g. a driver mechanism, by means of this down conductor. In order to establish a connection with the consumer, which as a rule lies outside the compartment 7, the down conductor 20a is run through the external wall of the compartment 7 or is embedded in it during molding or inserted during the process of injection molding the compartment 7, in such a way that a terminal piece of the down conductor 20a stands proud of the outer wall of the compartment 7, enabling a connection to a consumer to be plugged in, for example. The first contact spring 15 together with its holder may likewise be embedded in the wall of the compartment 7 during molding. It could just as easily be secured in the compartment 7 by means of a screw, adhesive, by welding or by similar means. It would also be conceivable for the first contact spring 15 to be made as a single component together with the down conductor, in which case it forms the cover or a part of the cover of the compartment 7 and is inserted in the body of the compartment 7, e.g. bonded.

Likewise disposed on the compartment 7, standing proud of the surface, is another down conductor 20b, which is connected to a second contact spring 16. Like the first contact spring 15, this second contact spring 16 may lie in the compartment 7. By preference, the second contact spring 16 lies in the compartment 7 opposite the first contact spring 15, i.e. the mid-points of the two contact surfaces of the contact springs 15, 16 lie essentially on an axis, e.g. the longitudinal axis of the compartment 7 and extend essentially parallel with one another. The directions in which the first contact spring 15 and the second contact spring 16 can be biased are therefore opposite one another. The spring path of the two contact springs 15, 16 is therefore essentially the same. It is particularly preferable if the second contact spring 16 is secured to the cover 18, as is the case in the embodiment illustrated as an example.

The clearance distance between the contact surface of the first contact spring 15 and the contact surface of the second contact spring 16 is shorter than the length (meaning the distance between the foremost tip of the terminal and the foremost tip of the opposite terminal) of the power source which can be positioned between the contact surfaces. By preference, it is smaller than the length of the power source plus the spring path of one of the contact springs 15, 16. When the power source is biased in the longitudinal direction, this will ensure a reliable contact between the terminals of the power source at all times, even if the power source has a moment of inertia which is different from that of the device or parts of it, due to its relatively high specific weight.

In order to connect the second contact spring 16 via the down conductor 29b to the consumer, a tape of conductive material is attached to a major part of the length of the compartment 7, on or in its internal wall, in the embodiment illustrated as an example here, and is connected to a ring of likewise conductive material provided in the peripheral direction in the bottom region of the compartment 7. When the cap is screwed on, this ring is in contact with indentations 19a of a crown-shaped connecting element 19, which is made from conductive material and is mounted on the cap 19. This connecting element is in turn connected to the second contact spring 16 so that when the power source is inserted, power can be transmitted from the second contact spring 16 via the connecting element 19 and the down conductor 20b to the consumer.

The down conductor 20b need not necessarily be provided in the form of a tape of conductive material, as a wire, with or without insulating sheath, a thin strip or any other connecting geometry would also fall within the scope of this invention. Similarly, the down conductor need not necessarily run through the compartment 7 and instead, a run could be molded entirely in the wall of the compartment 7 or a run along the external wall of the compartments 7 would also be conceivable. It is merely necessary to ensure that the entire down conductor 20b is disposed inside the sealed housing of the device and a reliable connection to a consumer can be established. Equally, the ring disposed in the peripheral direction mentioned above need not necessarily be a closed ring. As long as it is guaranteed that the connecting element 19, which will be described in more detail below, can reliably establish a contact with the down conductor 20b when the cap 18 is fitted, it may be provided in the form of a part-ring, the extension of the tape itself or a dot-shaped contact point or any other shape of contact surface. In order to establish the requisite contact between the connecting element 19 and down conductor 20b reliably, the last part of the down conductor 20b may also be provided in the form of an increasing material thickness or may project into the compartment 7 due to the shape imparted to the internal wall of the compartment 7 in the region of the connecting element 19.

Figure 5:
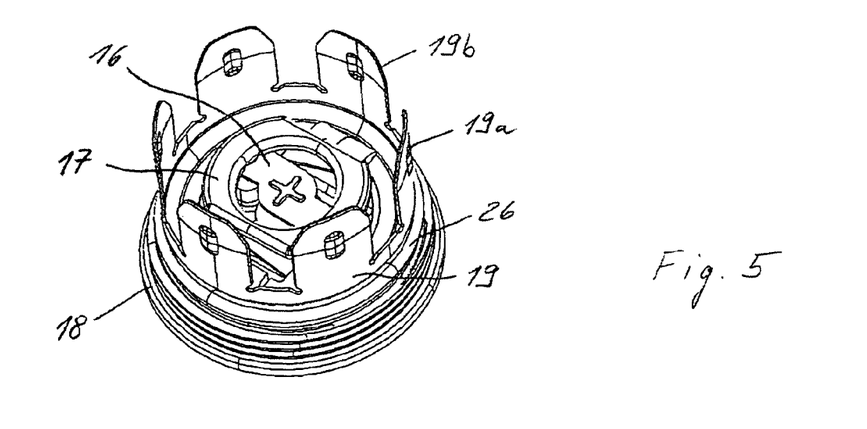
FIG. 5 shows a contact spring integrated in a cover of the battery compartment.

The above-mentioned cap 18 is illustrated in detail in FIG. 5. It essentially consists of a base body with an external thread. This thread fits exactly in the internal thread formed in the access opening 8 of the compartment 7. In the screwed-on state, the cap 18 closes off the compartment 7, and preferably closes it off so that it is watertight. The base body has a side, which is not visible here, which forms the external face of the device in the screwed-on state and may have a locating feature for stowing a cap tool to enable the cap 18 to be firmly pulled on. Attached to the oppositely lying side of the base body, i.e. the side which lies in the interior of the compartment 7 when the cap 18 is screwed on, is the above-mentioned connecting part 19. It may be attached by means of a screw or rivet connection, a bonded or welded connection, a clamp or some other mechanical connection or any other type of connection that will guarantee a reliable connection of the connecting element 19 to the cap 18.

A sealing ring 26 may be inserted between the cap 18 and the connecting element 19 to provide additional sealing. This sealing ring 26 is squashed in the compartment 7 when the cap 19 is firmly screwed on and thus improves the sealing action of the screw connection.

In the embodiment illustrated as an example here, the connecting element 19 is crown-shaped, i.e. several extensions 19b standing vertically proud of the base body are disposed in a circle about the mid-axis of the cap 18. The extensions 19b are connected to one another in the region of the connection with the cap 18 and are also spaced uniformly apart. The extensions may have a simple rectangular shape, with oblique ends, as is the case in the embodiment illustrated as an example, or may be semi-circular, for example. At their top part, i.e. remote from the cap 18, they may have indentations 19a, which are formed by indenting the material of the connecting element 19, for example. The diameter of the circle formed by the extensions 19b is large enough for the power source to be engaged by the extensions 19b in this region.

Disposed in the interior of the crown formed by the connecting element 19 is the second contact spring 16. As with the first contact spring 15, it may be provided in the form of a leaf spring, coil spring, helical spring or bending spring. It stands proud of the cap 18 in the direction towards the interior of the compartment 7 and is able to spring inwards in the opposite direction, i.e. against the cap 18. The second contact spring 16 is conductingly connected to the connecting element 19. This can be achieved using an appropriate connection between the second contact spring 16 and connecting element 19, e.g. a soldered connection, although it would also be conceivable for the connecting element 19 and the contact spring 16 to be made as a single part, in which case it may be made from a thin metal sheet, for example, by an appropriate punching and forming process.

As described above, the power source is connected to the down conductor 20b via the second contact spring 16 and the connecting element 19. If, as is the case in the embodiment illustrated as an example here, the contact is established between the connecting part 19 or its extensions 19b and a ring-shaped metal tape of the down conductor 20b, it may be of advantage to bias the extensions 19b with a radial pre-tensioning force, preferably a pre-tensioning force that is directed radially outwards. This pre-tensioning, either alone or in conjunction with the power source accommodated in the crown formed by the extensions 19b, ensures or ensure a reliable contact.

Instead of the crown illustrated, the connecting element may have only one extension 19b or any number of extensions 19b. If a circle of tape in the interior of the compartment 7 is used as the counter-contact, it will still be possible to establish a reliable contact with only one extension 19b. However, the contact of the down conductor 20b could also extend over only a part of the periphery of the internal wall of the compartment 7 or could be provided in the form of a tape or strip. In the latter case, a reliable contact can still be guaranteed if the connecting element 19 is provided in the form of a closed circle. The decisive factor is that when the cap 18 is firmly screwed on, a contact always exists between the connecting element 19 and the down conductor 20b, by means of which power can be transmitted to a consumer.

In order to prevent failure or incorrect functioning of the device due to incorrect positioning of the power source in the compartment 7, a mispoling protector 17 may be provided. This mispoling protector 17 is made from a non-conducting material and is applied, e.g. bonded, directly to one of the contact springs 15, 16. The mispoling protector may basically be of any shape, but preferably has an annular shape or the shape of a flat, circular disc. This being the case, the thickness of the ring or circular disc is big enough for the projecting opposite terminal, in the case of a battery for example, to project through the hole in the middle of the ring or disc up to the second contact spring 16. If the battery is inserted incorrectly, the mispoling protector 17 must reliably prevent contact between the contact spring 16 and the flat terminal.

Figure 6:
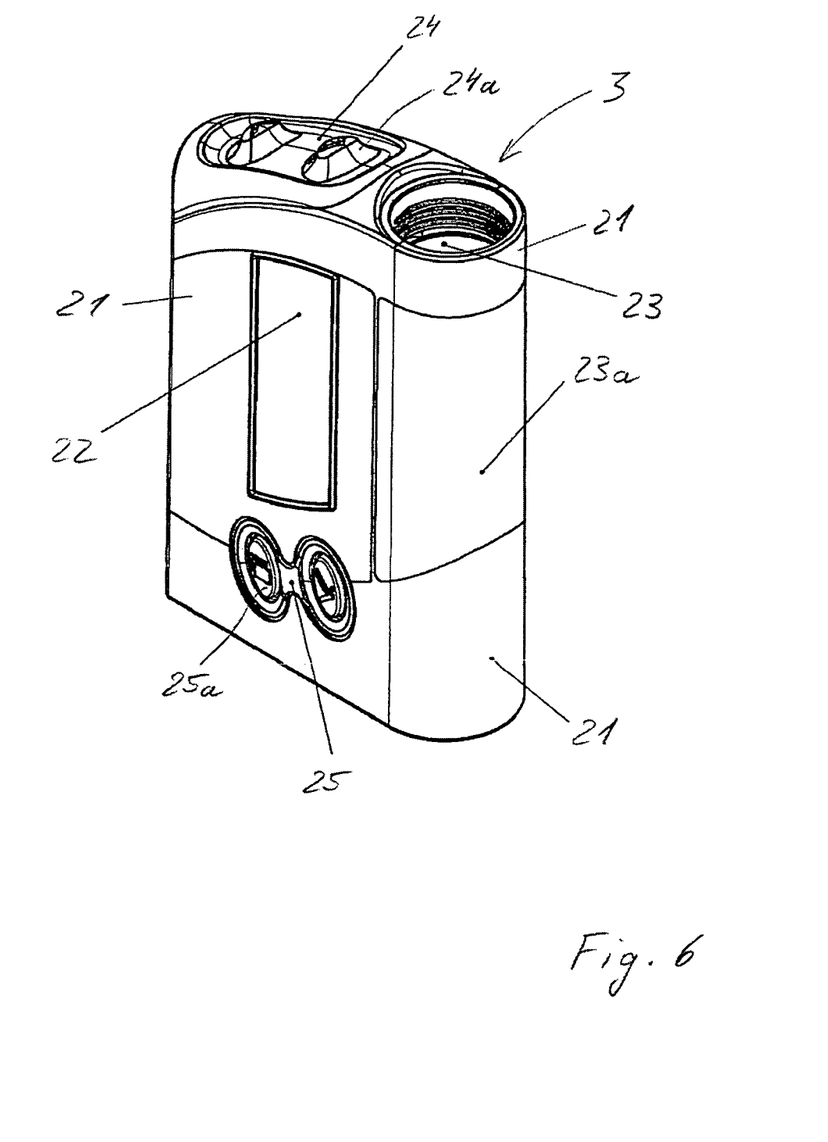
FIG. 6 is a perspective view of the other of the housing shells.

FIG. 6 illustrates the first housing shell 1 in a state immediately after production before the infusion device is assembled. Housing shell 1 forms the side walls and the major part of an upper terminal wall of the housing 1, 2. The shell structure 21 is oval in cross-section with two parallel side walls and two cylindrical, in the embodiment illustrated as an example circular cylindrical, side walls connecting the parallel side walls. The oval hollow cross-section is completely open at the bottom face, where it is closed off by the second housing shell 2 when the infusion device is in the assembled state, as described above. In addition to the open bottom face, the housing shell 1 has only one other opening, namely an opening of the receiver 3 remote from the bottom face. The product container can be inserted in the receiver 3 through the opening. The opening can be closed by means of a screw cap and O-sealing ring, rendering it watertight. The housing shell 1 is watertight with the exception of the two openings.

Insofar as the housing shell 1 forms the external wall of the housing 1, 2, it comprises a shell structure 21, two transparent wall regions 22 and 23a and two flexible wall regions 24 and 25. The wall region 22 is a display window. The wall region 23a forms a larger part of the external wall of the receiver 3 and the wall regions 24 and 25 screen two control fields, each with two control elements. The control elements are push buttons. The wall regions 24 and 25 each have an indentation for each control element, respectively an indentation 24*a* and 25*a*. The shape of the indentations 24*a* and 25*a* is adapted to the shape of the respective control element. A three-dimensional structure is imparted to the wall regions 24 and 25 as a result of the indentations 24*a* and 25*a*, which matches the structure of the respective control field. The control elements behind the wall region 25 are used as a means of controlling a display, for example for retrieving specific information. The control elements behind the wall region 24 are used for controlling the infusion device, for example for selecting a specific bolus. The wall regions 24 and 25 are so flexible that they enable the control elements to be operated without any difficulty.

The shell structure 21 forms a type of skeleton for the housing shell 1. It is made from a plastic material, which is solid and hard enough to provide a dimensionally stable case in spite of having only a slim wall thickness in the range of tenths of a millimeter, which protects the components accommodated in the housing shell 1 from the mechanical stress which can be expected during operation.

The plastic material of the shell structure 21 may be impermeable to light. The wall regions 22 and 23*a*, on the other hand, are made from a transparent plastic material to enable the display to be read and to ensure that the level control of the product container is visible.

The wall regions 22, 23*a*, 24 and 25 fill the openings of the shell structure 21. The wall regions 22 to 25 are intrinsically watertight and are connected to the shell structure 21 along the edge of the respective opening of the shell structure 21 around the periphery in a continuous watertight fit.

The housing shell 1 is made by a multi-component injection molding process. For molding purposes, the injection mold used has a cavity matching the shape of the housing shell 1, which is filled with molding material. The wall regions 22 and 23 are also formed by injection molding before the shell structure 21 is molded, and the wall region 22 is made as a flat thin disc. The wall region 23*a* forms a circular tube, which is entirely made from the transparent plastic material and not only forms the transparent wall region 23*a* of the housing external wall but also forms the side wall of the receiver 3 peripherally.

To make the housing shell 1 by the injection molding process, the wall region 22 and the tube 23 are placed in the injection mold. To make the shell structure 21 by the injection molding process, fillers are also placed in the injection mold in place of the wall regions 24 and 25, each of which has the same shape as the opening to be formed in the shell structure 21. Once the fillers and the insert parts 22 and 23 have been positioned, the injection mold is closed and the material of the shell structure 21 is injected in. The plastic material of the shell structure 21 is injected around the insert part 22 along its side edge. Around the insert part 23, the injection takes place on both of its end faces across an arcuate region in each case. The plastic material of the shell structure 21 also adjoins the external face of the insert part 23 in two longitudinal strips and is connected to this external face along the two strips, rendering it watertight.

An injection then takes place in the same manner around the wall regions 22 and 23*a*, rendering them watertight, and once the plastic material of the shell structure 21 has cured, the injection mold is opened and the fillers removed. The injection mold is then closed again. In a final step of the injection molding process, the elastomeric plastic material is injected through nozzles that were previously closed into the cavities in the injection mold produced by the fillers, where it is injected onto the shell structure 21. As a result of the latter injection, a watertight connection is produced, extending continuously along the edge of the respective opening of the shell structure 21. The flexible wall regions 24 and 25 are connected to the respective opening edge of the shell structure 21 in a watertight fit along their outer edge due to a combination of the form fit and the material join. The watertight connection of the transparent wall regions 22 and 23*a* to the shell structure 21 is also essentially based on a material join and form fit between the two plastic materials.

In a preferred variant of the method, the housing shell 2 is produced entirely with one injection mold, with the exception of the insert parts 22 and 23, which are produced beforehand in a separate injection mold or are each produced in a separate injection mold. Once the pre-molded insert parts 22 and 23 have been placed in the injection mold for making the housing shell 2, the injection mold is closed and the second plastic material is injected around the insert parts 22 and 23. The injection mold then opens and the core of the injection mold together with the shell structure 21 and the insert parts 22 and 23 rotates into a second cavity in the same mold. Before the injection mold closes again, the insert parts 22 and 23 for the next housing shell 2 are placed in the first cavity, which is now free again. Once the mold has closed, the second plastic material is injected around the insert parts 22 and 23 in the first cavity again. In the second cavity, the soft components 24 and 25, i.e. the elastic wall regions, are simultaneously injected. Once the injection mold has opened and the finished housing shell 2 has been ejected from the first cavity and insert parts 22 and 23 have been placed in the first cavity again, the "carousel" starts again.

REFERENCE NUMBERS

1 First housing shell
2 Second housing shell
3 Receiver
4 Conveying mechanism
4*a* Plunger rod
4*b* Drive member
4*c* Drive member
5 Seal gap
6 Support structure
6*a* Region of material join
6*b* Raised area
7 Battery compartment
8 Access opening
9 Holder
10 Seal
11 Shell region
12 Base
13 Sealing lip
14 Anchoring element
15 Contact spring
16 Contact spring
17 Mispoling protector
18 Cap
19 Connecting element
19*a* Projection, indentation
19*b* Extension
20*a* Down conductor
20*b* Down conductor
21 Shell structure
22 Insert part, transparent wall region
23 Insert part
23*a* Transparent wall region
24 Flexible wall region
24*a* Indentation
25 Flexible wall region 25a Indentation
26 Sealing ring
B Gap width
V Forward drive direction

What is claimed is:

1. A method of producing an administering device for infusing or injecting a liquid medicament, comprising:
   providing an injection mold which defines a first housing shell, wherein the first housing shell is configured to accommodate components which comprises a receiver for the liquid medicament, a conveying mechanism, and a control element, wherein the first housing shell defines a first opening, a second opening for the control element, a third opening through which the components are inserted in the first housing shell when the administering device is assembled, and a seal gap which extends around the third opening;
   providing to the injection mold, a pre-molded insert part which forms a transparent, watertight wall region made from a first plastic material;
   injecting into the injection mold a different, second plastic material so that the first plastic material and the second plastic material are joined to together along an edge of the first opening in a watertight fit by an injection mold formed seal, wherein the first opening is closed by the pre-molded insert part and the second plastic material forms side walls of the first housing shell;
   providing the components in the first housing shell through the third opening;
   injecting into the injection mold onto the second plastic material a different, third plastic material so that the third plastic material and the second plastic material are joined together along an edge of the second opening in a watertight fit by an injection mold formed seal, wherein the third plastic material forms a flexible, watertight wall region which closes the second opening and overlaps the control element;
   providing a dimensionally stable support structure having an anchoring element to the third opening of the first housing shell; and
   injection molding a thermoplastic elastomer over the dimensionally stable support structure to form a second housing shell which surrounds the anchoring element and into the seal gap of the first housing shell both to close the third opening and form a seal therebetween with a formed sealing lip such that the first housing shell and second housing shell are connected in a watertight fit.

2. The method as claimed in claim 1, further comprises providing the first housing shell and second housing shell in a generally oval in cross-section.

3. The method as claimed in claim 1, further comprises providing the flexible wall region as a three-dimensional structure adapted to a shape of the control element.

4. The method as claimed in claim 1, further comprises providing the flexible wall region with an indentation into which the control element projects.

5. The method as claimed in 4, further comprises providing the control element as a push button.

6. The method as claimed in claim 4, further comprises molding the flexible wall region from a thermoplastic elastomer.

7. The method as claimed in claim 1, wherein the insert part is generally tubular and said method comprises providing a shell region of the insert part forming the transparent wall region.

8. The method as claimed in claim 7, further comprises providing the transparent wall region as a display window or an external wall of the receiver for the liquid medicament.

9. The method as claimed in claim 8, wherein the first housing shell comprises several transparent wall regions, one of which is the display window and another of which forms the external wall of the receiver for the liquid medicament, and said method comprises providing the wall regions as respectively watertight insert parts around which the first plastic material is injected.

10. The method as claimed in claim 1, further comprises joining the seal in a form fit and material join onto a shell structure.

11. The method as claimed in claim 1, further comprises joining the dimensionally stable support structure and a holder in a form and non-positive fit.

12. The method as claimed in claim 11, wherein the conveying mechanism comprises a drive member which is supported on the holder in a forward drive direction and transversely thereto in a radial direction.

13. The method as claimed in claim 1, further comprises providing in the seal gap the sealing lip which establishes a pressing contact with each oppositely lying, mutually facing side walls of the seal gap.

14. A method of producing an administering device for infusing or injecting a liquid medicament, comprising:
   providing a first housing shell, wherein the first housing shell comprises:
      a receiver for the liquid medicament, wherein the receiver comprises a first opening for receiving the liquid medicament,
      a conveying mechanism configured to convey the liquid medicament in a forward drive direction,
      a second opening at a terminal end of the first housing shell, and
      a seal gap which extends around the second opening at the terminal end of the first housing shell;
   providing a dimensionally stable support structure having an anchoring element to the second opening of the first housing shell;
   injection molding a thermoplastic elastomer over the dimensionally stable support structure to form a second housing shell which surrounds the anchoring element and into the seal gap of the first housing shell both to close the second opening and form a seal therebetween with a formed sealing lip such that the first housing shell and second housing shell are non-detachably connected in a watertight fit.

15. The method of claim 14, wherein the seal gap comprises side walls having a gap width narrower than the sealing lip such that when the second housing shell closes the second opening of the first housing shell the sealing lip sits in pressing contact with the side walls of the seal gap.

16. The method as claimed in claim 14, further comprises joining the dimensionally stable support structure and a holder in a form and non-positive fit.

17. The method of claim 16, wherein the conveying mechanism comprises a drive member which is supported on the holder in the forward drive direction and transversely thereto in a radial direction.

18. The method of claim 14, wherein the dimensionally stable support structure is a support frame for the seal and axial support for the sealing lip.

19. The method of claim 14, wherein the seal further forms a shell region at a bottom face of the second housing shell.

20. The method of claim 19, wherein the shell region acts as a damping means and anti-slip means on the bottom face of the second housing shell.

* * * * *

UNITED STATES PATENT AND TRADEMARK OFFICE
CERTIFICATE OF CORRECTION

| | | |
|---|---|---|
| PATENT NO. | : 8,652,387 B2 | Page 1 of 2 |
| APPLICATION NO. | : 13/406887 | |
| DATED | : February 18, 2014 | |
| INVENTOR(S) | : Philip Etter et al. | |

It is certified that error appears in the above-identified patent and that said Letters Patent is hereby corrected as shown below:

In the Specification

Col. 6, Line 55,
"engages round an outer peripheral edge on the top face of the" should read
--engages around an outer peripheral edge on the top face of the--;

Col. 6, Line 57,
"only engages round the support structure 6 but also engages" should read
--only engages around the support structure 6 but also engages--;

Col. 6, Line 67,
"engages round the support structure 6 and advantageously" should read
--engages around the support structure 6 and advantageously--;

Col. 7, Line 11,
"The support structure 6 not only acts a support frame for the" should read
--The support structure 6 not only acts as a support frame for the--;

In the Claims

Col. 13, Claim 1, Line 24,
"plastic material are joined to together along an edge of" should read
--plastic material are joined together along an edge of--;

Col. 13, Claim 5, Line 59,
"The method as claimed in 4, further comprises providing" should read
--The method as claimed in claim 4, further comprises providing--;

Signed and Sealed this
Twentieth Day of January, 2015

Michelle K. Lee
*Deputy Director of the United States Patent and Trademark Office*

CERTIFICATE OF CORRECTION (continued)
U.S. Pat. No. 8,652,387 B2

Col. 14, Claim 15, Line 51,
"The method of claim 14, wherein the seal gap com-" should read
--The method as claimed in claim 14, wherein the seal gap com- --;

Col. 14, Claim 17, Line 59,
"The method of claim 16, wherein the conveying mecha-" should read
--The method as claimed in claim 16, wherein the conveying mecha- --;

Col. 14, Claim 18, Line 63,
"The method of claim 14, wherein the dimensionally" should read
--The method as claimed in claim 14, wherein the dimensionally--;

Col. 14, Claim 19, Line 66,
"The method of claim 14, wherein the seal further forms" should read
--The method as claimed in claim 14, wherein the seal further forms--; and Col. 15, Claim 20, Line 1,
"The method of claim 19, wherein the shell region acts" should read
--The method as claimed in claim 19, wherein the shell region acts--.